(12) United States Patent
Lee et al.

(10) Patent No.: US 9,146,191 B2
(45) Date of Patent: Sep. 29, 2015

(54) GAS DETECTION SYSTEM AND RADIATION EMITTING DEVICE FOR THE GAS DETECTION SYSTEM

(71) Applicant: National Taiwan University, Taipei (TW)

(72) Inventors: Si-Chen Lee, Taipei (TW); Hung-Hsin Chen, Taipei (TW); Chun-Han Chen, Changhua (TW); Shang-Ru Tsai, Taichung (TW); Shi-Ming Lin, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 247 days.

(21) Appl. No.: 13/846,283

(22) Filed: Mar. 18, 2013

(65) Prior Publication Data

US 2014/0131581 A1    May 15, 2014

(30) Foreign Application Priority Data

Nov. 15, 2012 (TW) .............................. 101142677 A (51) Int. Cl.
| | |
|---|---|
| *G01J 5/02* | (2006.01) |
| *G01N 21/3504* | (2014.01) |
| *G01J 3/10* | (2006.01) |
| *G01N 21/35* | (2014.01) |
| *G01J 3/12* | (2006.01) |

(52) U.S. Cl.
CPC .............. *G01N 21/3504* (2013.01); *G01J 3/10* (2013.01); *G01J 2003/1213* (2013.01); *G01J 2003/1282* (2013.01); *G01N 21/35* (2013.01)

(58) Field of Classification Search
USPC .......................................................... 250/343
See application file for complete search history.

(56) References Cited

U.S. PATENT DOCUMENTS

| | | | | |
|---|---|---|---|---|
| 8,859,303 B2* | 10/2014 | Udrea et al. | ..................... | 438/22 |
| 2007/0131863 A1* | 6/2007 | Ellis et al. | ..................... | 250/343 |
| 2007/0290189 A1 | 12/2007 | Lee et al. | | |
| 2010/0213492 A1* | 8/2010 | Lee et al. | ......................... | 257/98 |
| 2011/0174799 A1* | 7/2011 | Ali et al. | .................... | 219/446.1 |

FOREIGN PATENT DOCUMENTS

| | | |
|---|---|---|
| TW | I297224 B | 5/2008 |
| TW | 200905283 A1 | 2/2009 |

* cited by examiner

*Primary Examiner* — Christine Sung
(74) *Attorney, Agent, or Firm* — Huffman Law Group, PC (57) ABSTRACT

A gas detection system comprising a case having a hollow chamber, a gas input port, a gas output port, a radiation emitting device, and a photo detector. The gas input port may be disposed on the case for a test gas flowing into the chamber. The gas output port may be disposed on the case for the test gas flowing out of the chamber. The radiation emitting device may be disposed on the case and operated in a surface plasmonic mode or a waveguide mode for emitting a narrow bandwidth thermal radiation light source with multi-peak wavelengths into the chamber, wherein the multi-peak wavelengths may comprise a first absorption wavelength and a second absorption wavelength of the test gas. The photo detector may be disposed on the case for detecting light intensity of the light source passing through the chamber to determine the concentration of the test gas.

29 Claims, 9 Drawing Sheets

GAS DETECTION SYSTEM AND RADIATION EMITTING DEVICE FOR THE GAS DETECTION SYSTEM

CROSS-REFERENCE TO RELATED APPLICATION(S)

This application claims priority to Taiwan Patent Application No. 101142677, filed on Nov. 15, 2012, the disclosure of which is hereby incorporated by reference in its entirety.

BACKGROUND OF THE DISCLOSURE

1. Field of the Invention

The present disclosure relates generally to a gas detection system. More specifically, the present disclosure relates to a gas detection system with a narrow bandwidth thermal radiation light emitting device as a light source thereof.

2. Description of the Related Art

A conventional gas detection system may be used to detect ambient gases in a house, a public place, or a working place. Accordingly, one may monitor concentration changes of ambient gases, especially toxic gases. A gas detection system may also be used as a medical test for the breath of a patient. Accordingly, one may diagnose the patient's disease or illness.

A gas detection system may usually be applied by using a chemical method or an optical method. Gas detection systems using chemical methods may often have slow response times. Further, gas detection systems using chemical methods may require that the absorbing material used for detection be replaced after a period of usage. Accordingly, the replacement of the absorbing material may increase costs and inconvenience. On the other hand, gas detection systems using optical methods may often comprise a broadband light source and a filter arranged in a complex structure. As one of ordinary skill in the art having the benefit of the present disclosure would appreciate, this may result in higher costs. Further, gas detection systems using only one filter may filter light with only one wavelength or a band of wavelengths. Such gas detection systems may not filter a light with more than one wavelength at the same time. Therefore, the conventional gas detection systems using optical methods belong to a single-beam optical sensor. Further, the filtering bandwidth of the filter is hard to reduce, which may affect the detection precision.

As one of ordinary skill in the art having the benefit of the present disclosure would appreciate, the absorption wavelength peak of some test gases or compounds may not always be a single peak. Thus, conventional gas detection systems may not be able to detect the multi-peak wavelengths. As a result, the detection precision and accuracy may be affected. Accordingly, there is a need for an improved gas detection system with high precision and accuracy.

SUMMARY OF THE DISCLOSURE

The present disclosure relates to a gas detection system that may use a narrow bandwidth thermal radiation light emitting device with single wavelength or multi-wavelengths as a light source.

In some embodiments, a gas detection system is provided. The gas detection system may comprise a case, a gas input port, a gas output port, a radiation emitting device, and a photo detector. The case may have a hollow chamber. The gas input port, the gas output port, the radiation emitting device, and the photo detector may be disposed on the case. The gas input port may provide for a test gas to flow into the chamber. The gas output port may provide for the test gas to flow out of the chamber. The radiation emitting device may be operated in a surface plasmonic mode or a waveguide mode for emitting a narrow bandwidth thermal radiation light source with multi-peak wavelengths into the chamber, in which the multi-peak wavelengths to comprise a first absorption wavelength and a second absorption wavelength of the test gas. The photo detector may be configured to detect the light intensity of the light source passing through the chamber in order to determine the concentration of the test gas.

In some embodiments, a radiation emitting device for a gas detection system is provided. The radiation emitting device may comprise a substrate, a first metal layer, a second metal layer, a first dielectric layer, a third metal layer, a second dielectric layer, and a fourth metal layer. The substrate may have a first surface and a second surface opposite to the first surface. The first metal layer may be disposed on the first surface and may be connected to a current for heating the radiation emitting device. The second metal layer may be disposed on the second surface. The first dielectric layer may be disposed on the second metal layer. The third metal layer may be disposed on the first dielectric layer and may have a first periodic structure. The second dielectric layer may be disposed on the third metal layer. The fourth metal layer may be disposed on the second dielectric layer and may have a second periodic structure. The radiation emitting device operated in a surface plasmonic mode or a waveguide mode for emitting a narrow bandwidth thermal radiation light source with single-peak wavelength or multi-peak wavelengths.

Accordingly, the present disclosure may advantageously provide for reducing the gas detection system size by removing the filter and provide for detecting all wavelength peaks for specific gases in order to distinguish the type and concentration of the test gases more precisely and accurately than conventional gas detection systems. According to some embodiments of the present disclosure, the light source of the gas detection system may have a narrow bandwidth wavelength, which is beneficial for analysis by computer software after noise reduction.

The foregoing is a summary and shall not be construed to limit the scope of the claims. The operations and devices disclosed herein may be implemented in a number of ways, and such changes and modifications may be made without departing from this disclosure and its broader aspects. Other aspects, inventive features, and advantages of the disclosure, as defined solely by the claims, are described in the non-limiting detailed description set forth below.

BRIEF DESCRIPTION OF THE DRAWINGS

Exemplary embodiments will be more readily understood from the following detailed description when read in conjunction with the appended drawing, in which:

FIG. 5($a$) illustrates a spectrum of the radiation emitting device for the gas detection system according to an embodiment of the present disclosure.

FIG. 5($b$) illustrates a spectrum of the radiation emitting device for the gas detection system according to an embodiment of the present disclosure.

DETAILED DESCRIPTION OF EMBODIMENTS

Reference will be made in detail to the present embodiments, examples of which are illustrated in the accompanying drawings. Wherever possible, the same reference numbers are used in the drawings and the description to refer to the same or like parts. In the drawings, the shape and thickness of one embodiment may be exaggerated for clarity and convenience. This description will be directed in particular to elements forming part of, or cooperating more directly with, apparatus in accordance with the present disclosure. It is to be understood that elements not specifically shown or described may take various forms well known to those skilled in the art. Further, when a layer is referred to as being on another layer or "on" a substrate, it may be directly on the other layer or on the substrate, or intervening layers may also be present.

Figure 1A:
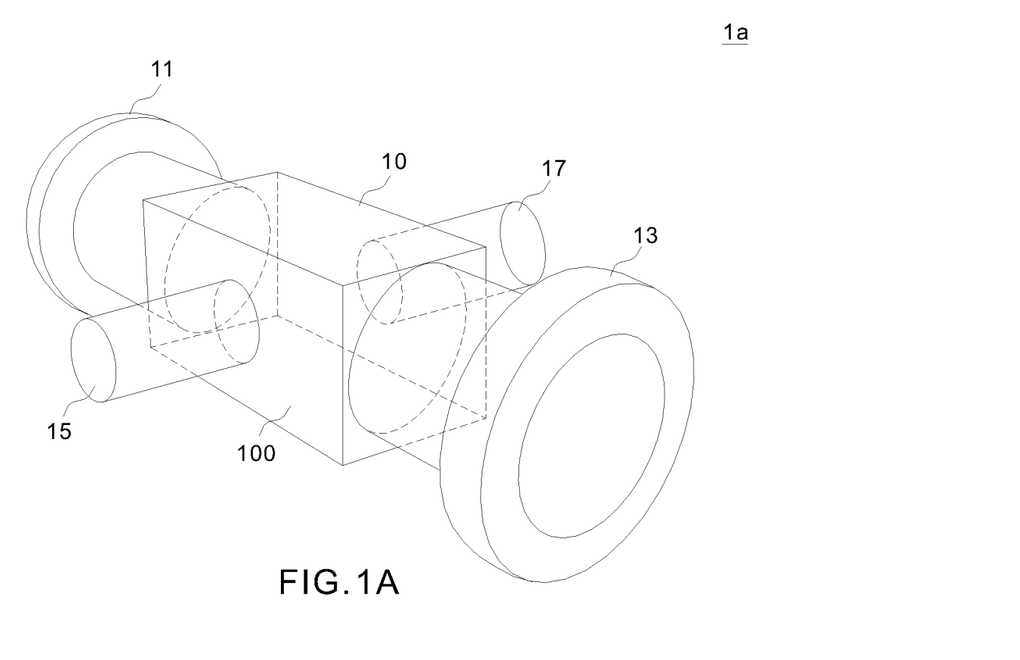
FIG. 1A illustrates a schematic diagram of the gas detection system according to an embodiment of the present disclosure.

Reference is now made to FIG. 1A. FIG. 1A is a schematic diagram illustrating a gas detection system according to one embodiment of the present disclosure. The gas detection system 1$a$ may comprise a case 10, a gas input port 11, a gas output port 13, a radiation emitting device 15, and a photo detector 17. The case 10 may comprise opacity material and may have a hollow chamber 100 inside of it. The case 10 may have the a cuboid appearance, comprising a plurality of exterior surfaces. The gas input port 11 may be disposed on a first surface of the case 10, and the gas input port 11 may be connected through the chamber 100 such that a test gas may flow into the chamber 100. The gas output port 13 may be disposed on a second surface of the case 10, and the gas output port 13 may be connected through the chamber 100 such that the test gas may flow out of the chamber 100. The second surface may be different from the first surface, or the second surface may be, but is not necessarily, opposite to the first surface.

The radiation emitting device 15 may be disposed on a third surface of the case 10, which may have a first opening connected through the chamber 100, such that the radiation emitting device 15 may emit a narrow bandwidth thermal radiation light source with single-peak or multi-peak wavelengths into the chamber 100. The photo detector 17 may be disposed on a fourth surface of the case 10 such that the photo detector 17 may sense the intensity of the light source passing through the chamber 100 to distinguish the type and concentration of the test gas precisely and accurately. The fourth surface may be different from the third surface, or the fourth surface may be, but is not necessarily, opposite to the third surface. More specifically, the photo detector 17 may receive the thermal radiation light after absorption by the test gas. Then, the photo detector 17 may convert the thermal radiation light into an electric signal such as voltage difference, which may indicate the intensity of the light passing through the chamber 100. In some embodiments, the photo detector 17 may have a thermopile.

As one of ordinary skill in the art having the benefit of the present to disclosure would appreciate, in the present disclosure, the term "narrow" in the "narrow" bandwidth thermal radiation light source with single-peak or multi-peak wavelengths emitted from the radiation emitting device 15 may mean the full width at half maximum (FWHM) of about 0.05 μm, or the ratio of FWHM and the peak of the wavelength of about or less than 10%.

As one of ordinary skill in the art having the benefit of the present disclosure would appreciate, the structure of the radiation emitting device 15 may be designed to emit the thermal radiation light source with single-peak or multi-peak wavelengths corresponding to the absorption wavelength of the test gas. Further, the wavelength of the thermal radiation may comprise a first absorption wavelength and a second absorption wavelength of the test gas. The number of the absorption wavelengths may not be limited to the ones mentioned above. For example, if the test gas is a single, the first absorption wavelength may be the primary absorption wavelength of the single gas, and the second absorption wavelength may be the minor absorption wavelength of the single gas. If the test gas is a mixing gas, the first absorption wavelength and the second absorption wavelength may correspond to the two primary absorption wavelengths of the mixing gas.

Figure 1B:
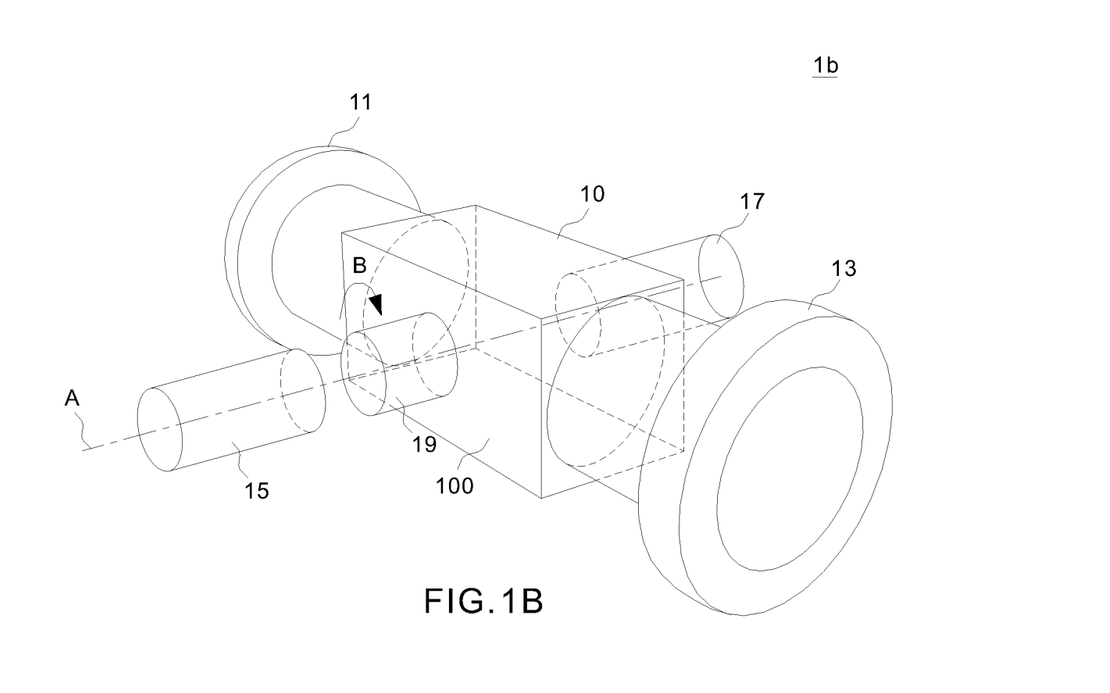
FIG. 1B illustrates a schematic diagram of the gas detection system according to an embodiment of the present disclosure.

Reference is now made to FIG. 1B. FIG. 1B is a schematic diagram depicting the gas detection system according to an embodiment of the present disclosure. As shown in FIG. 1B, the gas detection system 1$b$ may be similar to the gas detection system 1a. The gas detection system 1b may similarly comprise the case 10, the gas input port 11, the gas output port 13, the radiation emitting device 15, and the photo detector 17 in the same arrangement. One difference between the gas detection system 1b and the gas detection system 1a may be that the gas detection system 1b further comprises a polarizing filter 19 disposed on the case 10.

In some embodiments, the polarizing filter 19 may be capable of rotating between the radiation emitting device 15 and the case 10. Further, the polarizing filter 19 may be capable of rotating toward the direction B along the axis A which may be a common central axis of the radiation emitting device 15 and the polarizing filter 19. The rotation angle of the polarizing filter 19 may be about 90 degrees. When the narrow bandwidth thermal radiation light source with multi-peak wavelengths emitted from the radiation emitting device 15 has different polarizing directions, the polarizing filter 19 may filter the wavelength of the lighting source corresponding to the primary absorption wavelength of the test gas before the unfiltered lighting source passes through the chamber 100.

If the test gas is a single gas that may absorb a primary absorption wavelength and a minor absorption wavelength, the polarizing filter 19 may rotate in a first predetermined angle to pass the light source emitted from the radiation emitting device 15 with the primary absorption wavelength through the chamber 100 for detection by the photo detector 17. After the photo detector 17 detects the light source with the primary absorption wavelength, the polarizing filter 19 may rotate again in a second predetermined angle to pass the minor absorption wavelength through the chamber 100 for detection by the photo detector 17. Accordingly, a processor incorporated in or independent from the photo detector 17 may operate signal processing for the signal intensity corresponding to the detected light source with the main or minor absorption wavelength in order to estimate the type or concentration of the test gas. In some embodiments, the photo detector 17 may detect two wavelengths at the same time without the polarizing filter 19 and may also detect the background environment without a light source. Further, the processor may determine and estimate the type or concentration of the test gas by operating signal processing.

When the test gas is a mixing gas that may absorb at least two main absorption wavelengths including a first absorption wavelength and a second absorption wavelength, the polarizing filter 19 may rotate in a first predetermined angle to pass one of the light sources emitted from the radiation emitting device 15 with the two main absorption wavelengths (the first absorption wavelength) through the chamber 100 for detection by the photo detector 17. After the photo detector 17 detects the light source with the first absorption wavelength, the polarizing filter 19 may rotate again in a second predetermined angle to pass another one of the two main absorption wavelengths (the second absorption wavelength) through the chamber 100 for detection by the photo detector 17. Accordingly, a processor incorporated in or independent from the photo detector 17 may operate signal processing for the signal intensity corresponding to the detected light source with the main absorption wavelengths to estimate the type or concentration of the test gas. Therefore, the gas detection system 1b may obtain the concentration of at least two test gases in the chamber 100 via one light source (the radiation emitting device 15) and one sensor (the photo detector 17).

The gas detection system 1b may filter the narrow bandwidth thermal radiation light source with multi-peak wavelengths via the polarizing filter 19 in order to reduce any interference in the detection of the photo detector 17 for the main absorption wavelength caused by the absorption from the other gas in the chamber 100. Accordingly, the sensitivity and accuracy of the photo detector 17 may be increased.

As one of ordinary skill in the art having the benefit of the present disclosure would appreciate, in practice, the gas detection system 1b may use a narrow bandwidth thermal radiation light source with multi-peak wavelengths. Simultaneously, the detection sys polarizing filter 19 may filter a wavelength corresponding to the absorption wavelength of the test gas.

As one of ordinary skill in the art having the benefit of the present disclosure would appreciate, the radiation emitting device 15, according to some embodiments of the present disclosure, may emit the narrow bandwidth thermal radiation light source with multi-peak wavelengths. Thus, the radiation emitting device 15 may replace the use of two radiation emitting devices with different light sources with single-peak wavelengths. As a result, production costs for the gas detection system 1b may be reduced. Further, the narrow bandwidth thermal radiation light source with multi-peak wavelengths emitted from the radiation emitting device 15 may provide light energy with at least two bandwidths. Accordingly, this may improve the sensitivity and accuracy of the photo detector 17.

As one of ordinary skill in the art having the benefit of the present disclosure would appreciate, increasing the number of times of the detection for the gas and the signal processing could reduce noise effectively.

Figure 1C:
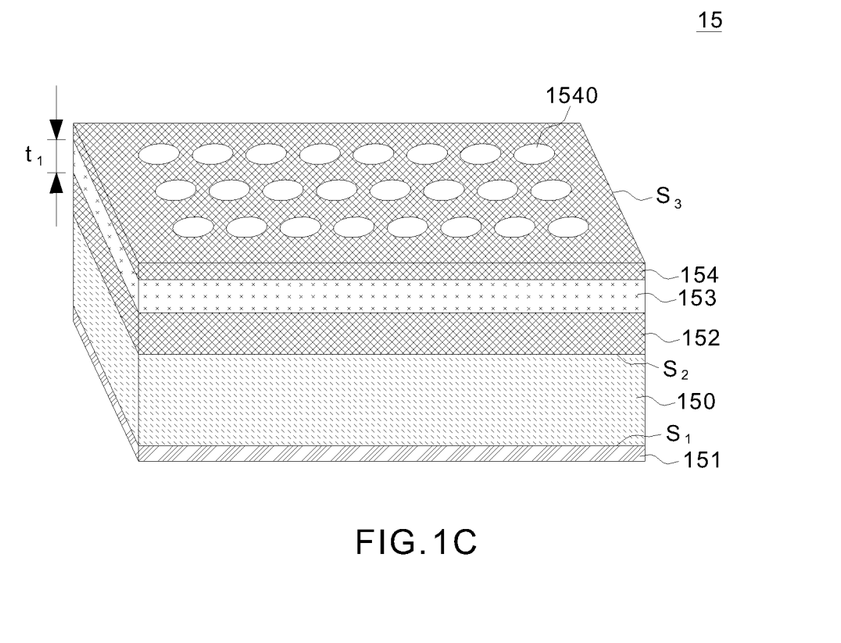
FIG. 1C illustrates a cross-sectional view of the radiation emitting device for the gas detection system according to an embodiment of the present disclosure.

Reference is now made to FIG. 1C. FIG. 1C illustrates a cross-sectional view of a radiation emitting device for a gas detection system according to one embodiment of the present disclosure. As shown in FIG. 1C, the radiation emitting device 15 may comprise a substrate 150, a first metal layer 151, a second metal layer 152, a first dielectric layer 153, and a second dielectric layer 154. The substrate 150 has a first surface $S_1$ and a second surface $S_2$, wherein the second surface $S_2$ may be opposite to the first surface $S_1$. The first metal layer 151 may be disposed on the first surface $S_1$, and the second metal layer 152 may be disposed on the second surface $S_2$. The first dielectric layer 153 may be disposed on the second metal layer 152, and the third metal layer 154 may be disposed on the first dielectric layer 153. The third metal layer 154 may have a first periodic structure 1540. The first periodic structure 1540 may be, but is not necessarily, a plurality of independent holes in the shape of rectangular or circular and arranged in a rectangular or hexagonal pattern as depicted in FIG. 1C.

As one of ordinary skill in the art having the benefit of the present disclosure would appreciate, the first metal layer 151 may be connected to a direct current so as to be at a high temperature as high impedance for heating the radiation emitting device 15. When the first dielectric layer 153 generates black body radiation resulting from high temperature and is then coupled to the surfaces of the second metal layer 152 and the third metal layer 154, the radiation emitting device 15 may operate in a surface plasmonic mode to emit the narrow bandwidth thermal radiation light source with single-peak or multi-peak wavelengths. The radiation emitting device 15 may also operate in a waveguide mode to emit the narrow bandwidth thermal radiation light source with single-peak or multi-peak wavelengths by restricting the light source between the second metal layer 152 and the third metal layer 154 and generating constructive interference.

As one of ordinary skill in the art having the benefit of the present disclosure would appreciate, when the two ends of the first metal layer 151 are connected with the current regarded as a heat source, the second metal layer 152 may restrain or obstruct the background radiation emitted from the substrate 150 and reflect or couple the heat radiation emitted from the first dielectric layer 153. Accordingly, the first dielectric layer 153 may be the heat radiation light source or heat radiation waveguide. The first dielectric layer 153 and the third metal layer 154 may form a metal/dielectric interface. The third metal layer 154 may couple with the surface plasmonic mode from the upper surface $S_3$ of the third metal layer 154 and air, the surface plasmonic mode from the third metal layer 154 and the first dielectric layer 153, or reflect the waveguide mode from the first dielectric layer 153.

In one embodiment, the substrate 150 may be, but is not necessarily limited to, a semi-conducive substrate, a glass substrate, or an insulated substrate. The first layer 151 may comprise molybdenum (Mo), gold (Au), tungsten (W), chromium (Cr), or other heat resistant conductive material. The second metal layer 152 and the third metal layer 154 may comprise gold (Au), silver (Ag), aluminum (Al), platinum (Pt), chromium (Cr), titanium (Ti), tungsten (W), tantalum (Ta), copper (Cu), cobalt (Co), nickel (Ni), iron (Fe), molybdenum (Mo), or other metal material with high reflectivity. The first dielectric layer 153 may be oxide or nitride, such as $SiO_2$, SiN, $MgF_2$, $Al_2O_3$, or $TiO_2$.

As one of ordinary skill in the art having the benefit of the present disclosure would appreciate, the emitting mechanism of the radiation emitting device 15 may be operating in one or two of the surface plasmonic mode and/or the waveguide mode. Whether the light source emitted from the radiation emitting device 15 has a single-peak or multi-peak may be determined by the thickness $t_1$ of the first dielectric layer 153 and the shape and size of the first periodic structure 1540. The type of the light source emitted from the radiation emitting device 15 may be determined by the material of the first dielectric layer 153. Further, light source with multi-peaks in different polarizations may be obtained by designing the structure of the radiation emitting device 15.

Reference is now made to FIGS. 2A-2E. FIGS. 2A-2E are cross-sectional views illustrating the portion of a radiation emitting device for a gas detection system according to an embodiment of the present disclosure. For clear representation, the radiation emitting devices 25a-25e in FIGS. 2A to 2E only depict the second metal layer 252, the first dielectric layer 253, and the third metal layer 254. Other layers may be identified in FIG. 1C.

Figure 2A:
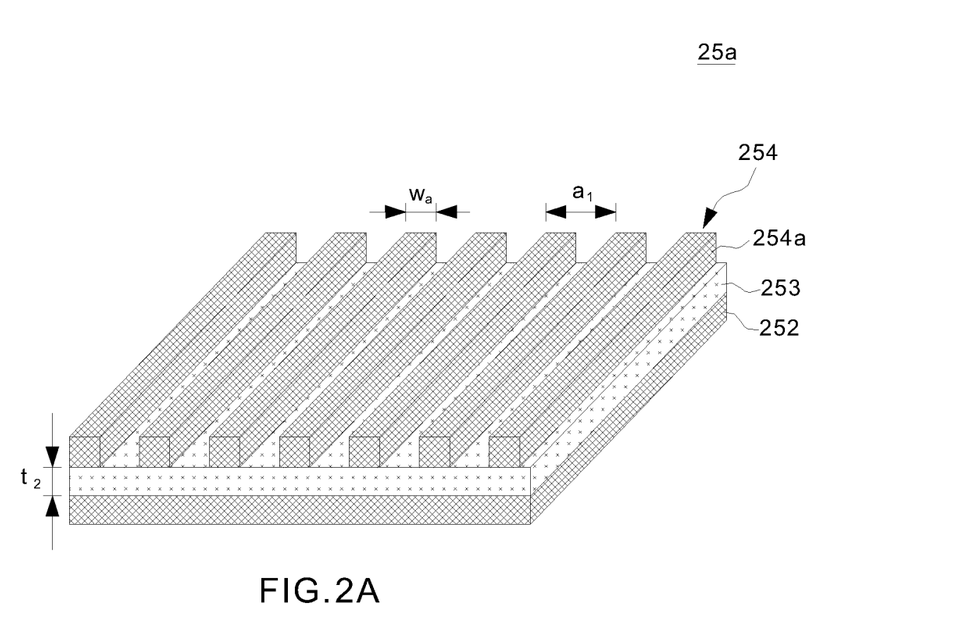
FIG. 2A illustrates a cross-sectional view of a portion of the radiation emitting device for the gas detection system according to an embodiment of the present disclosure.
Figure 2B:
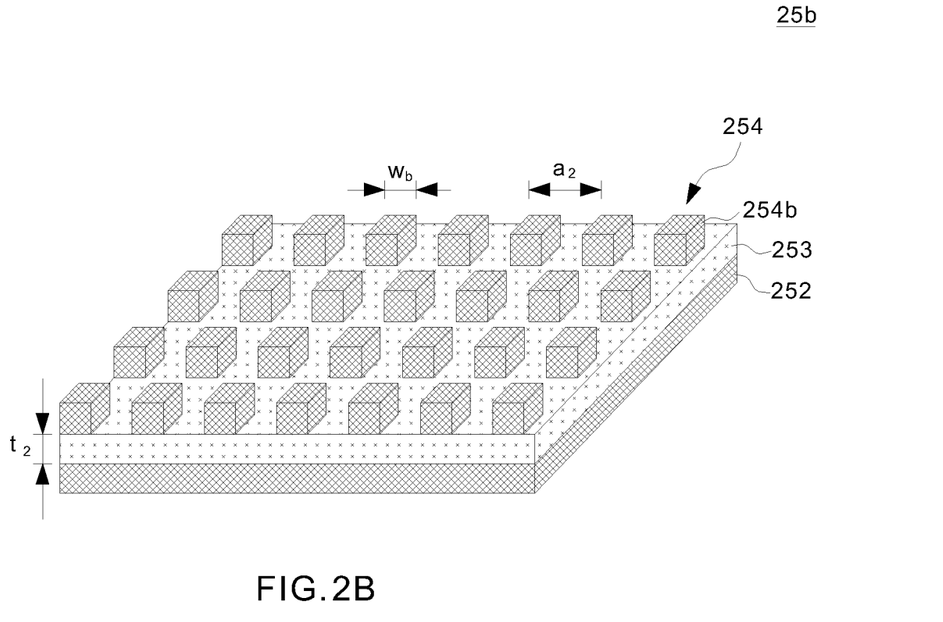
FIG. 2B illustrates a cross-sectional view of a portion of the radiation emitting device for the gas detection system according to an embodiment of the present disclosure.
Figure 2C:
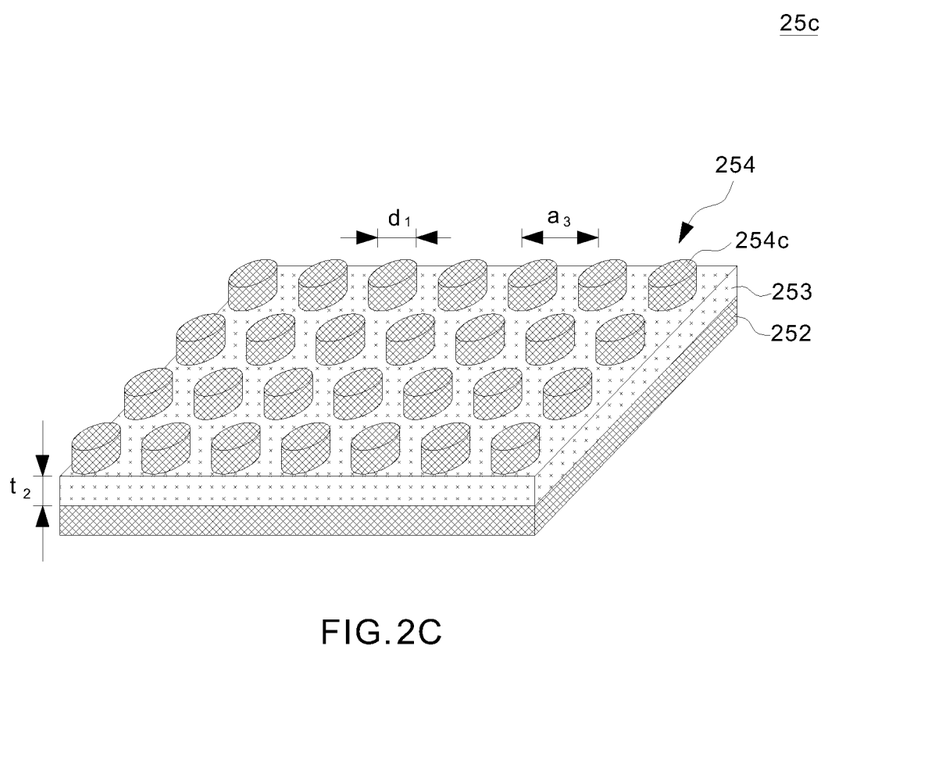
FIG. 2C illustrates a cross-sectional view of a portion of the radiation emitting device for the gas detection system according to an embodiment of the present disclosure.
Figure 2D:
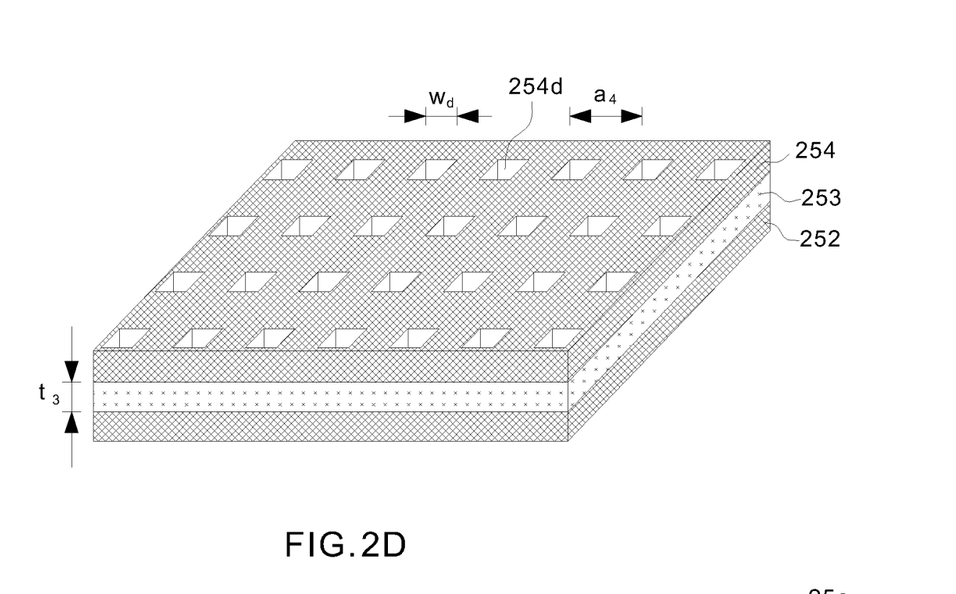
FIG. 2D illustrates a cross-sectional view of a portion of the radiation emitting device for the gas detection system according to an embodiment of the present disclosure.
Figure 2E:
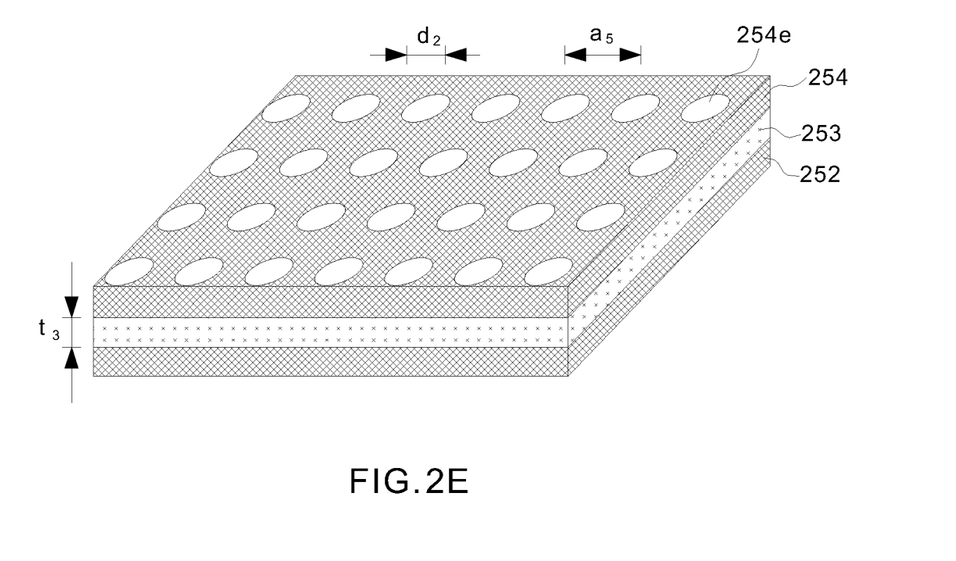
FIG. 2E illustrates a cross-sectional view of a portion of the radiation emitting device for the gas detection system according to an embodiment of the present disclosure.

Roughly, the third metal layers 254 of the radiation emitting devices 25a-25e having the first periodic structures 254a-254e may be classified in two types. One type is the first periodic structures 254a-254c as shown in FIGS. 2A to 2C, which may have a plurality of blocks independent of one another. Another type is the first periodic structures 254d-254e as shown in FIGS. 2D to 2E, which may have a plurality of holes in a continuous structure. The radiation emitting devices 25a-25e may operate in three modes comprising a localized surface plasmonic mode (LSP mode), a surface plasmonic mode (SP mode), and a waveguide mode (WM) according to the thickness $t_2$ of the first periodic structures 254a-254e and the thickness $t_3$ of the first dielectric layer 253.

As shown in FIG. 2A, the third metal layer 254 of the radiation emitting device 25a may have a first periodic structure 254a in a one dimensional and elongated shape. The period $a_1$ of the first periodic structure 254a may be between about 1 µm and about 10 µm. The width $w_a$ of each elongated structure of the first periodic structure 254a may be between about 1 µm and about 5 µm. The thickness $t_2$ of the first dielectric layer 253 may be between about 0.1 nm and about 400 nm.

As shown in FIG. 2B, the third metal layer 254 of the radiation emitting device 25b may have a first periodic structure 254b in a cubic shape. The period $a_2$ of the first periodic structure 254b may be between about 1 µm and about 10 µm. The cubic structures of the first periodic structure 254b may be arranged in square, hexagon, or irregular patterns. The width $w_b$ of each cubic structure of the first periodic structure 254b may be between about 1 µm and about 5 µm. The thickness $t_2$ of the first dielectric layer 253 may be between about 0.1 nm and about 400 nm.

As shown in FIG. 2C, the third metal layer 254 of the radiation emitting device 25c may have a first periodic structure 254c in a cylindrical shape. The period $a_3$ of the first periodic structure 254c may be between about 1 µm and about 10 µm. The cylindrical structures of the first periodic structure 254c may be arranged in square, hexagon, or irregular patterns. The diameter $d_1$ of each cylindrical structure of the first periodic structure 254c may be between about 1 µm and about 5 µm. The thickness $t_2$ of the first dielectric layer 253 may be between about 0.1 nm and about 400 nm.

The above-mentioned radiation emitting devices 25a-25c may operate in LSP mode. Said radiation emitting devices 25a-25c may emit light sources with different wavelengths between about 2 µm and about 8 µm according to the sizes of the first periodic structures 254a-254c such as $w_a$, $w_b$, $d_1$. The sizes of the first periodic structure 254a-254c such as $w_a$, $w_b$, $d_1$ may be proportional to the wavelength of the light sources emitted from the radiation emitting devices 25a-25c. Additionally, the thickness $t_2$ and refractive index of the first dielectric layer 253 may be proportional to the wavelength of light source emitted from the radiation emitting devices 25a-25c.

As shown in FIG. 2D, the third metal layer 254 of the radiation emitting device 25d may have a first periodic structure 254d including a plurality of holes in a square shape. The period $a_4$ of the first periodic structure 254d may be between about 1 µm and about 10 µm. The width $w_d$ of each hole structure of the first periodic structure 254d may be between about 1 µm and about 4 µm. Besides, the thickness $t_3$ of the first dielectric layer 253 may be between about 0.1 nm and about 3 µm.

As shown in FIG. 2E, the third metal layer 254 of the radiation emitting device 25e may have a first periodic structure 254e including a plurality of holes in a circular shape. The period $a_5$ of the first periodic structure 254e may be between about 1 µm and about 10 µm. The diameter $d_2$ of each hole structure of the first periodic structure 254e may be between about 1 µm and about 4 µm. Besides, the thickness $t_3$ of the first dielectric layer 253 may be between about 0.1 nm and about 3 µm.

When the thickness $t_3$ of the first dielectric layers 253 of the radiation emitting devices 25d, 25e is between 0.1 nm and 3 µm, the radiation emitting devices 25d, 25e may operate in SP mode. The radiation emitting devices 25d, 25e may emit light sources with different wavelengths between about 2 µm and about 8 µm according to the period of the first periodic structures 254d, 254e such as $a_4$, $a_5$. The periods of the first periodic structure 254d, 254e such as $a_4$, $a_5$ may be proportional to the wavelength of light source emitted from the radiation emitting devices 25d, 25e. Further, the refractive index of the first dielectric layer 253 may be proportional to the wavelength of the light source emitted from the radiation emitting devices 25d, 25e.

Moreover, when the thickness $t_3$ of the first dielectric layers 253 of the radiation emitting devices 25d, 25e is between about 0.1 nm and about 3 µm, the radiation emitting devices 25d, 25e may operate in WM. The radiation emitting devices 25*d*, 25*e* may emit light sources with different wavelength between about 2 μm and about 8 μm according to the thickness $t_3$ and the refractive index of the first dielectric layers 253. The thickness $t_3$ may be proportional to the wavelength of light source emitted from the radiation emitting devices 25*d*, 25*e*. As one of ordinary skill in the art having the benefit of the present disclosure would appreciate, this proportionality may be presented through the equation: $\lambda=2*n*t_3$. In this equation, $\lambda$ denotes the peak wavelength of the light source, and n denotes the refractive index of the first dielectric layer 253. For example, the refractive index of the first dielectric layer 253 having $SiO_2$ is about 1.4. Further, as one of ordinary skill in the art having the benefit of the present disclosure would appreciate, the SP mode and WM may coexist with each other.

Figure 3A:
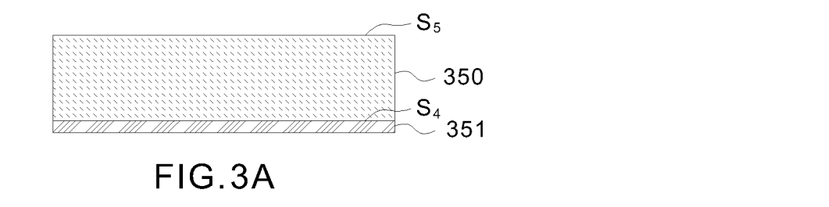
FIG. 3A illustrates a cross-sectional view of the production process of the radiation emitting device for the gas detection system according to an embodiment of the present disclosure.
Figure 3B:
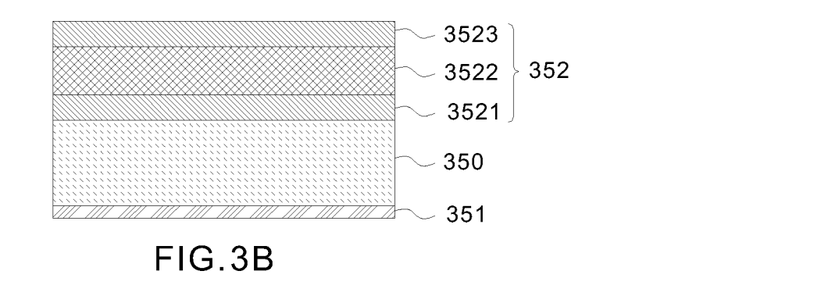
FIG. 3B illustrates a cross-sectional view of the production process of the radiation emitting device for the gas detection system according to an embodiment of the present disclosure.

Reference is now made to FIGS. 3A to 3D. FIGS. 3A to 3D illustrate cross-sectional views of the production process of the radiation emitting device for the gas detection system according to some embodiments of the present disclosure. Initially, the production process may comprise providing a substrate 350 having a first surface $S_4$ and a second surface $S_5$ opposite to the first surface $S_4$, and vapor depositing or coating a first metal layer 351 on the first surface $S_4$ as shown in FIG. 3A. Then, the production process comprises vapor depositing or coating a second metal layer 352 on the second surface $S_5$ as shown in FIG. 3B, in which the thickness of the second metal layer 352 may be about 100 nm. In one embodiment, the second metal layer 352 may comprise a metal layer 3522 and at least one adhesive layer such as two adhesive layers 3521, 3523 disposed on the two opposite sides of the metal layer 3522. The material of the adhesive layers 3521, 3523 may comprise titanium (Ti). As one of ordinary skill in the art having the benefit of the present disclosure would appreciate, no particular order for depositing the first metal layer 351 and the second metal layer 352 may be required.

Figure 3C:
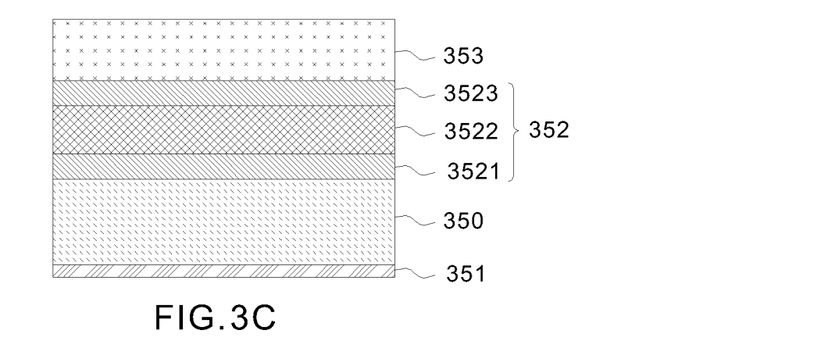
FIG. 3C illustrates a cross-sectional view of the production process of the radiation emitting device for the gas detection system according to an embodiment of the present disclosure.
Figure 3D:
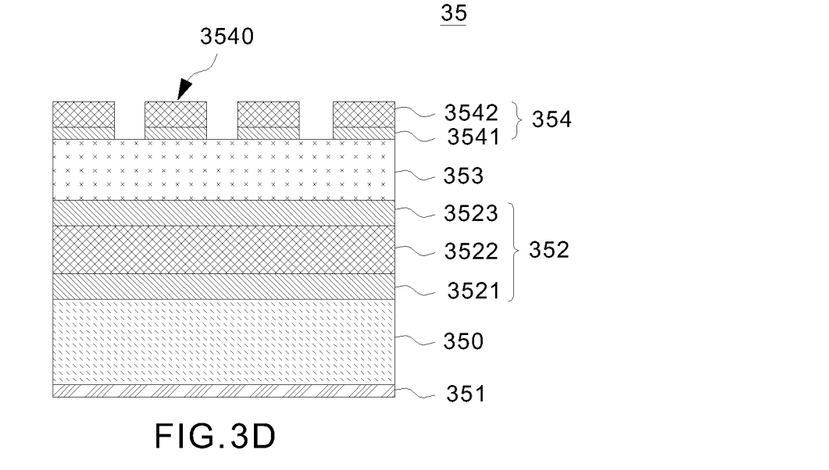
FIG. 3D illustrates a cross-sectional view of the production process of the radiation emitting device for the gas detection system according to an embodiment of the present disclosure.

After that, the production process may comprise vapor depositing or coating a first dielectric layer 353 on the second metal layer 352 as shown in FIG. 3C. Finally, the production process may comprise forming a third metal layer 354 having a first periodic structure 3540 on the first dielectric layer 353 by photolithography as shown in FIG. 3D. The configuration and arrangement of the first periodic structure 3540 is described in the paragraphs herein corresponding to FIGS. 2A to 2E. In one embodiment, the third metal layer 354 may comprise a metal layer 3542 and an adhesive layer 3541. The adhesive layer 3541 may be disposed between the first dielectric layer 353 and the metal layer 3542. The material of the adhesive layer 3541 may be titanium (Ti).

The first metal layer 351 may comprise molybdenum (Mo), gold (Au), tungsten (W), chromium (Cr), or other heat resistant conductive material. The second metal layer 352 and the third metal layer 354 may comprise gold (Au), silver (Ag), aluminum (Al), platinum (Pt), chromium (Cr), titanium (Ti), tungsten (W), tantalum (Ta), copper (Cu), cobalt (Co), nickel (Ni), iron (Fe), molybdenum (Mo), or other metal with high reflectivity respectively. The material of the first dielectric layer 353 may comprise Oxide or Nitride, such as $SiO_2$, SiN, $MgF_2$, $Al_2O_3$, or $TiO_2$. Accordingly, the radiation emitting device 35 may emit light source adjustably in accordance with the descriptions corresponding to FIGS. 2A to 2E.

Figure 4A:
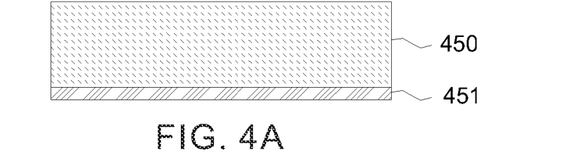
FIG. 4A illustrates a cross-sectional view of the production process of the radiation emitting device for the gas detection system according to an embodiment of the present disclosure.
Figure 4B:
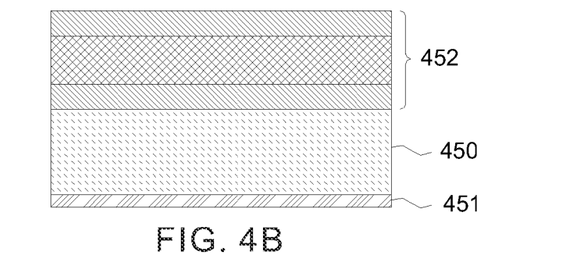
FIG. 4B illustrates a cross-sectional view of the production process of the radiation emitting device for the gas detection system according to an embodiment of the present disclosure.
Figure 4C:
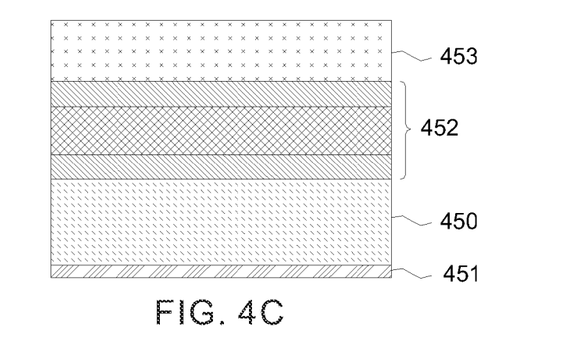
FIG. 4C illustrates a cross-sectional view of the production process of the radiation emitting device for the gas detection system according to an embodiment of the present disclosure.
Figure 4D:
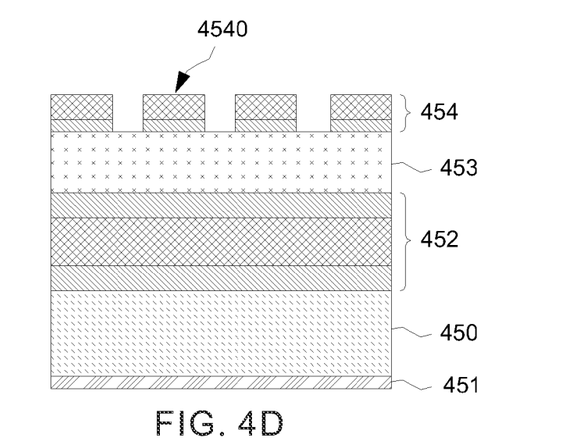
FIG. 4D illustrates a cross-sectional view of the production process of the radiation emitting device for the gas detection system according to an embodiment of the present disclosure.

Reference is now made to FIGS. 4A to 4F. FIGS. 4A to 4F illustrate cross-sectional views of the production process of a radiation emitting device for a gas detection system according to an embodiment of the present disclosure. The production process of the radiation emitting device 45 may be similar to that of the radiation emitting device 35. The production process of the radiation emitting device 45 may comprise vapor depositing or coating a first metal layer 451 and the second metal layer 452 on the opposite sides of the substrate 450 as shown in FIGS. 4A to 4B, vapor depositing or coating a first dielectric layer 453 on the second metal layer 452 as shown in FIG. 4C, and forming a third metal layer 454 having a first periodic structure 4540 on the first dielectric layer 453 by photolithography as shown in FIG. 4D.

Figure 4E:
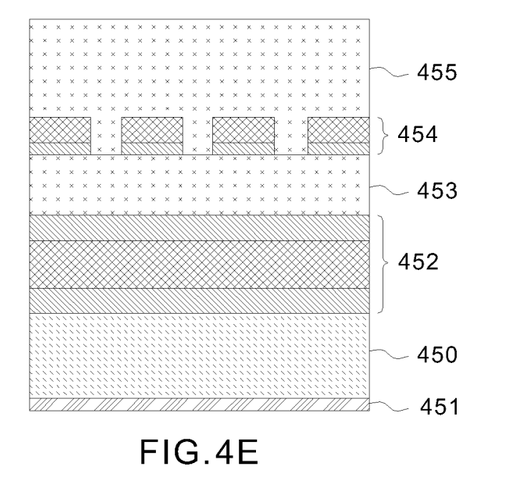
FIG. 4E illustrates a cross-sectional view of the production process of the radiation emitting device for the gas detection system according to an embodiment of the present disclosure.
Figure 4F:
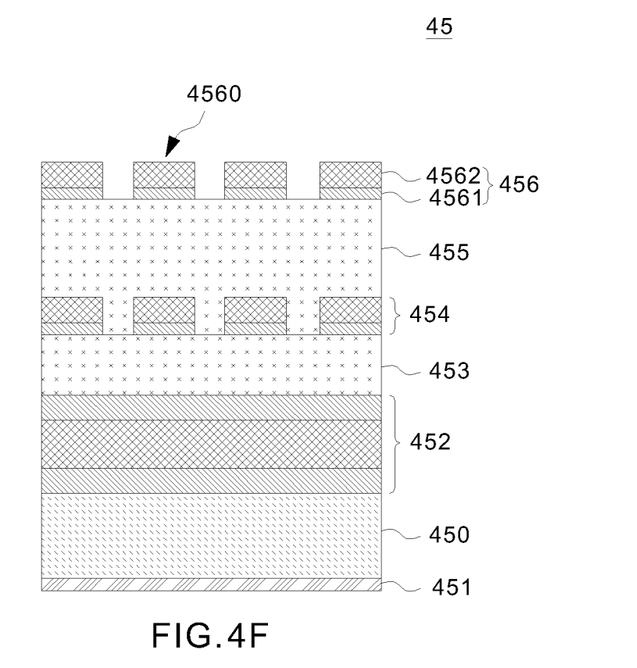
FIG. 4F illustrates a cross-sectional view of the production process of the radiation emitting device for the gas detection system according to an embodiment of the present disclosure.

An example difference between the production process of the radiation emitting device 45 and that of the radiation emitting device 35 is that the production process of the radiation emitting device 45 may further comprise vapor depositing a second dielectric layer 455 on the third metal layer 454 as shown in FIG. 4E, and forming a fourth metal layer 456 having a second periodic structure 4560 on the second to dielectric layer 455 by photolithography as shown in FIG. 4F. The configuration and arrangement of the second periodic structure 4560 are described in the paragraphs herein corresponding to FIGS. 2A to 2E. In some embodiments, the fourth metal layer 456 may comprise a metal layer 4562 and an adhesive layer 4561. The material of the metal layer 4562 may be the same as that of the second metal layer 452 or the third metal layer 454. The adhesive layer 4561 may be disposed between the second dielectric 455 and the metal layer 4562. The material of the adhesive layer 4561 may comprise Ti. Accordingly, the radiation emitting device 45 may emit different a light source by adjusting the thicknesses of the first dielectric layer 453 and the second dielectric layer 455, and adjusting the size and shape of the first periodic structure 4540 and the second periodic structure 4560. The adjusting methods are described in the paragraphs herein corresponding to FIGS. 2A to 2E.

As one of ordinary skill in the art having the benefit of the present disclosure would appreciate, the narrow bandwidth thermal radiation light source with multi-peak wavelengths emitted from the radiation emitting devices 25*a*-25*e*, 35, 45 may be determined by adjusting the structural parameters of the radiation emitting devices 25*a*-25*e*, 35, 45 for different test gases corresponding to single absorption wavelengths or multi absorption wavelengths. The radiation emitting devices 25*a*-25*e*, 35, 45 may not emit light with non-absorption wavelengths of the test gas such that the interference to the accuracy of the photo detector 17 for the non-absorption wavelength may be reduced.

Figure 5:
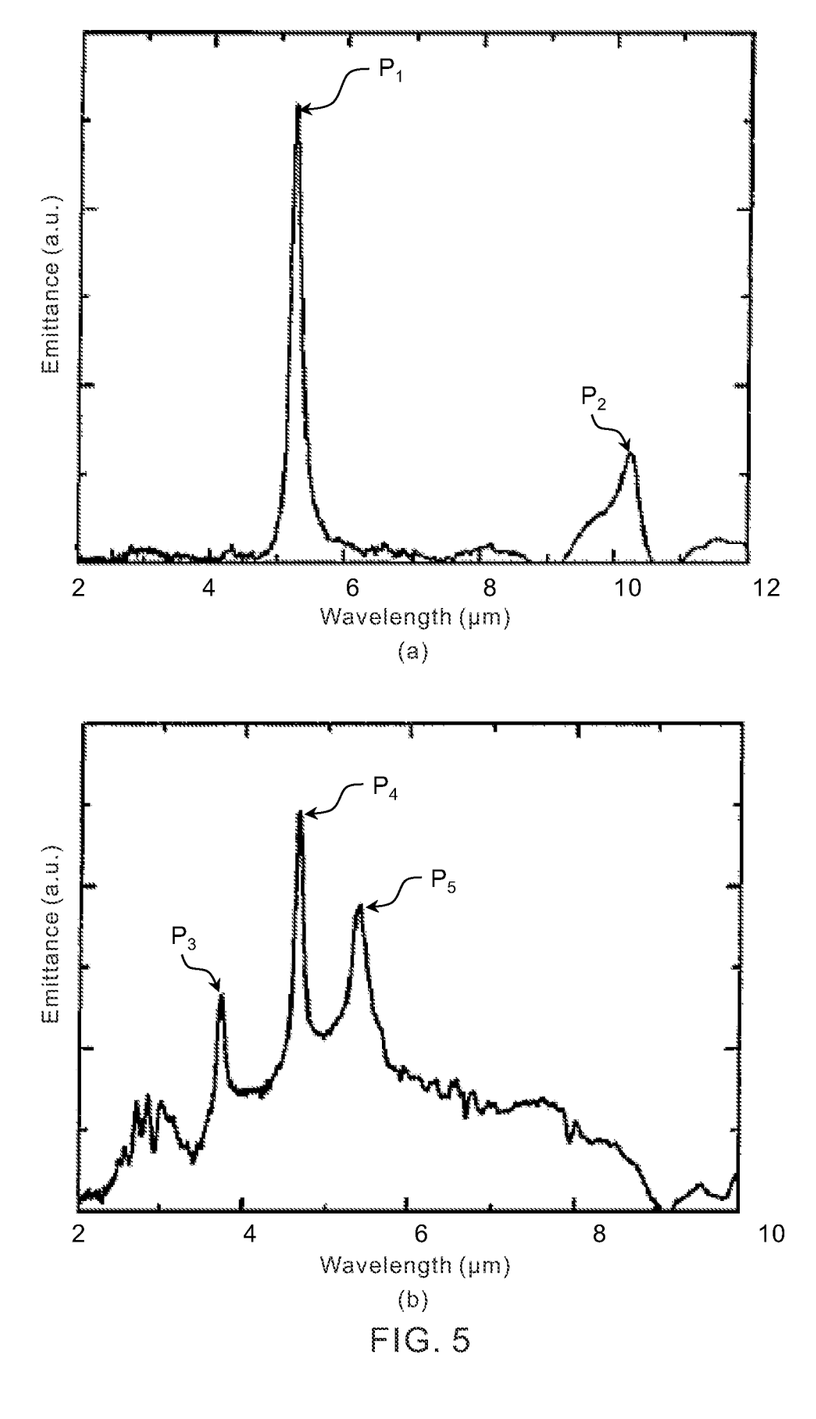

Reference is now made to FIG. 5(*a*)-5(*b*). FIGS. 5(*a*)-5(*b*) illustrate spectra of a radiation emitting device for a gas detection system according to an embodiment of the present disclosure. The radiation emitting device 35 may emit the light source in the spectrum as shown in FIG. 5(*a*), in which the main narrow bandwidth wavelength has the peak $P_1$ at about 5 μm, and the minor narrow bandwidth wavelength has the peak $P_2$ at about 10 μm. The radiation emitting device 45 with double periodic structures may emit the light source in the spectrum as shown in FIG. 5(*b*), in which a plurality of narrow bandwidth wavelengths have the peaks at $P_3$, $P_4$, $P_5$ at about 3.8 μm, about 4.5 μm, and about 5.3 μm, respectively. The light source may not be limited to the above-mentioned narrow bandwidth wavelengths, which may be adjusted between about 3 μm and about 8 μm by changing the structure parameters.

Figure 6:
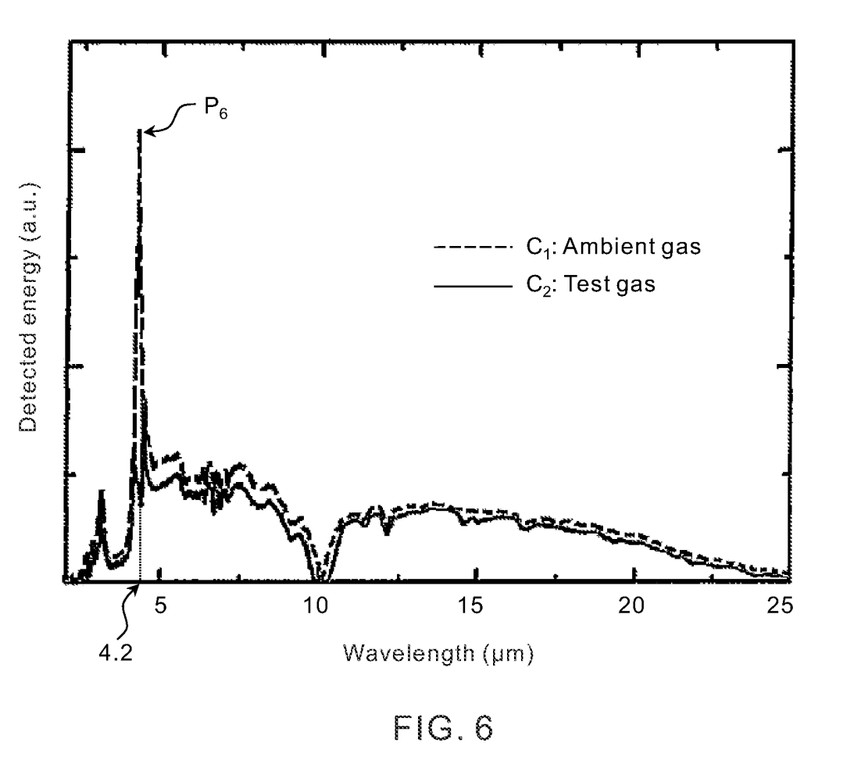
FIG. 6 illustrates a spectrum of the detection energy for the gas detection system according to one embodiment of the present disclosure.

Reference is now made to FIG. 6. FIG. 6 illustrates a spectrum of a detection energy for a gas detection system according to an embodiment of the present disclosure. The two curves presented are that of the detected energy distribution of the light source passing through the chamber and that detected by the photo detector. The curve $C_1$ denotes the spectrum of the light source detected by the photo detector after passing the chamber filled with ambient gas. The curve $C_2$ denotes the spectrum of the light source detected by the photo detector after passing the chamber filled with test gas. In one embodiment, the test gas may be $CO_2$, and the narrow bandwidth wavelength of the light source may have the peak $P_6$ at about 4.2 μm as shown in FIG. 6. Meanwhile, the curve $C_2$ has an obvious drop at about 4.2 μm, which means that the test gas may absorb the narrow bandwidth wavelength at about 4.2 μm. Accordingly, the processor may determine the concentration of the test gas based on the intensity of detected energy detected from the photo detector.

As one of ordinary skill in the art having the benefit of the present disclosure would appreciate, embodiments of the gas detection system of the present disclosure may use different materials and structures of the radiation emitting device operating in the localized surface plasmonic mode, the surface plasmonic mode, or the waveguide mode to emit a narrow bandwidth thermal radiation light source with single peak or multi-peak wavelengths according to the absorption wavelength of the test gas, in conjunction with the chamber and the photo detector. The photo detector may obtain the concentration of the test gas in the chamber by detecting the light intensity after the light source passes the chamber and is absorbed by the test gas. Hence, the gas detection system may detect the test gas for all absorption wavelengths at the same time, and then get the type and concentration of the test gas more accurately than the optical sensor with single light source. More particularly, the narrow bandwidth thermal radiation light source may have high specificity for the test gas so as to increase the accuracy of the detection. Accordingly, the gas detection system may use a common photo detector without the selectivity for the wavelength and a novel radiation emitting device to achieve the technical features related to the conventional gas detection system comprising a broadband light source and a filter with narrow bandwidth as follows: (a) saving the usage of the filter; (b) reducing the interference of the detection accuracy of the photo detector from the non-absorption wavelength; (c) rising the detection energy for the multi-specific wavelengths detected from the photo detector caused by the narrow bandwidth light source with multi-peaks. The production process of the radiation emitting device may be simple and low cost. The emitting light may be adjusted with multi wavelengths for different test gas by modifying the structure parameters.

Realizations in accordance with the present disclosure have been to described in the context of particular embodiments. These embodiments are meant to be illustrative and not limiting. Many variations, modifications, additions, and improvements are possible. Accordingly, plural instances may be provided for components described herein as a single instance. Structures and functionality presented as discrete components in the exemplary configurations may be implemented as a combined structure or component. These and other variations, modifications, additions, and improvements may fall within the scope of the disclosure as defined in the claims that follow.

What is claimed is:

1. A gas detection system, comprising:
a case, having a hollow chamber;
a gas input port, disposed on the case for a test gas flowing into the chamber;
a gas output port, disposed on the case for the test gas flowing out of the chamber;
a radiation emitting device, disposed on the case and operated in a surface plasmonic mode or a waveguide mode for emitting a narrow bandwidth thermal radiation light source with multi-peak wavelengths into the chamber, wherein the multi-peak wavelengths comprise a first absorption wavelength and a second absorption wavelength of the test gas;
a photo detector, disposed on the case for detecting the light intensity of the light source passing through the chamber to determine the concentration of the test gas;
wherein the radiation emitting device comprises: a base, having a first surface and a second surface opposite with each other; a first metal layer, disposed on the first surface and connected to a current for heating the radiation emitting device; a second metal layer, disposed on the second surface; a first dielectric layer, disposed on the second metal layer; and a third metal layer, disposed on the first dielectric layer, and having a first periodic structure; and
wherein the radiation emitting device comprises: a second dielectric layer, disposed on the third metal layer; and a fourth metal layer, disposed on the second dielectric layer, and having a second periodic structure.

2. The gas detection system according to claim 1, wherein the first metal layer comprises molybdenum (Mo), gold (Au), tungsten (W), or chromium (Cr).

3. The gas detection system according to claim 1, wherein the second metal layer and the third metal layer comprise gold (Au), silver (Ag), aluminum (Al), platinum (Pt), chromium (Cr), titanium (Ti), tungsten (W), tantalum (Ta), copper (Cu), cobalt (Co), nickel (Ni), iron (Fe), or molybdenum (Mo).

4. The gas detection system according to claim 1, wherein the first periodic structure comprises a plurality of blocks in elongated, cubic, or cylindrical shapes.

5. The gas detection system according to claim 4, wherein the thickness of the first dielectric layer is between about 0.1 nm and about 400 nm.

6. The gas detection system according to claim 5, wherein the dimension of the first periodic structure is between about 1 μm and about 10 μm.

7. The gas detection system according to claim 1, wherein the first periodic structure comprises a plurality of holes in rectangular or circular shapes.

8. The gas detection system according to claim 7, wherein the thickness of the first dielectric is between about 0.1 nm and about 3 μm.

9. The gas detection system according to claim 8, wherein the period of the first periodic structure is between about 1 μm and about 10 μm.

10. The gas detection system according to claim 1, wherein the first periodic structure comprises a plurality of blocks in elongated, cubic, or cylindrical shapes.

11. The gas detection system according to claim 10, wherein the thickness of the first dielectric layer is between about 0.1 nm and about 3 μm.

12. The gas detection system according to claim 11, wherein the dimension of the first periodic structure is between about 1 μm and about 10 μm.

13. The gas detection system according to claim 1, wherein the second periodic structure comprises a plurality of holes in rectangular or circular shapes.

14. The gas detection system according to claim 13, wherein the thickness of the second dielectric is between about 0.1 nm and about 3 μm.

15. The gas detection system according to claim 14, wherein the period of the second periodic structure is between about 1 μm and about 10 μm.

16. The gas detection system according to claim 1, wherein the fourth metal layer comprises gold (Au), silver (Ag), aluminum (Al), platinum (Pt), chromium (Cr), titanium (Ti), tungsten (W), tantalum (Ta), copper (Cu), cobalt (Co), nickel (Ni), iron (Fe), or molybdenum (Mo).

17. The gas detection system according to claim 1, further comprising a polarizing filter disposed between the radiation emitting device and the photo detector, and configured to filter the first absorption wavelength or the second absorption wavelength of the test gas.

18. The gas detection system according to claim 1, wherein the test gas is a single gas and the first absorption wavelength comprises a primary absorption wavelength of the single gas, and the second absorption wavelength comprises a minor absorption wavelength.

19. The gas detection system according to claim 1, wherein the test gas is a mixing gas, and the first absorption wavelength and the second absorption wavelength are corresponding to the two primary absorption wavelengths of the mixing gas, respectively.

20. A radiation emitting device for a gas detection system, comprising:
- a substrate, having a first surface and a second surface opposite with each other;
- a first metal layer, disposed on the first surface and connected to a current for heating the radiation emitting device;
- a second metal layer, disposed on the second surface;
- a first dielectric layer, disposed on the second metal layer;
- a third metal layer, disposed on the first dielectric layer and having a first periodic structure;
- a second dielectric layer, disposed on the third metal layer; and
- a fourth metal layer, disposed on the second dielectric layer and having a second periodic structure;
- wherein the radiation emitting device operated in a surface plasmonic mode or a waveguide mode for emitting a narrow bandwidth thermal radiation light source with single-peak wavelength or multi-peak wavelengths.

21. The radiation emitting device according to claim 20, wherein each of the first periodic structure and the second periodic structure comprises a plurality of blocks in elongated, cubic, or cylindrical shapes.

22. The radiation emitting device according to claim 21, wherein the thickness of the first dielectric layer and the thickness of the second dielectric layer are each between about 0.1 nm and about 3 μm.

23. The radiation emitting device according to claim 22, wherein the dimension of the first periodic structure and the dimension of the second periodic structure are each between about 1 μm and about 10 μm.

24. The radiation emitting device according to claim 20, wherein the first periodic structure and the second periodic structure comprise a plurality of independent holes in rectangular or circular shapes.

25. The radiation emitting device according to claim 24, wherein the thickness of the first dielectric layer and the thickness of the second dielectric layer are each between about 0.1 nm and about 3 μm.

26. The radiation emitting device according to claim 25, wherein the period of the first periodic structure and the period of the second periodic structure are each between about 1 μm and about 10 μm.

27. The radiation emitting device according to claim 24, wherein the thickness of the first dielectric layer and the thickness of the second dielectric layer are each between about 0.1 nm and about 3 μm.

28. The radiation emitting device according to claim 20, wherein the first metal layer comprises molybdenum (Mo), gold (Au), tungsten (W), or chromium (Cr).

29. The radiation emitting device according to claim 20, wherein each of the second metal layer, the third metal layer and the fourth metal layer comprises gold (Au), silver (Ag), aluminum (Al), platinum (Pt), chromium (Cr), titanium (Ti), tungsten (W), tantalum (Ta), copper (Cu), cobalt (Co), nickel (Ni), iron (Fe), or molybdenum (Mo).

* * * * *